(12) United States Patent
Alexandre et al.

(10) Patent No.: US 7,798,989 B2
(45) Date of Patent: Sep. 21, 2010

(54) NEEDLELESS SYRINGE PROVIDED WITH A DAMPING INJECTOR RECEPTACLE

(75) Inventors: Patrick Alexandre, Gray (FR); Georges Baud, La Crau (FR); Bernard Brouquieres, Toulon (FR); Laurent D'Emmanuelle, Toulon (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 1107 days.

(21) Appl. No.: 10/585,574

(22) PCT Filed: Jan. 11, 2005

(86) PCT No.: PCT/FR2005/000051

§ 371 (c)(1),
(2), (4) Date: Jul. 10, 2006

(87) PCT Pub. No.: WO2005/082438

PCT Pub. Date: Sep. 9, 2005

(65) Prior Publication Data

US 2008/0039780 A1    Feb. 14, 2008

(30) Foreign Application Priority Data

Jan. 27, 2004    (FR) .................................. 04 00721

(51) Int. Cl.
*A61M 5/30*    (2006.01)

(52) U.S. Cl. ........................................ 604/68

(58) Field of Classification Search ............. 604/68–70, 604/82, 500, 143–154
See application file for complete search history.

(56) References Cited

U.S. PATENT DOCUMENTS

| 6,004,287 A | * | 12/1999 | Loomis et al. ................. 604/68 |
| 2002/0035348 A1 | | 3/2002 | Hjertman |
| 2003/0050596 A1 | * | 3/2003 | Alexandre et al. ............ 604/69 |
| 2003/0149396 A1 | | 8/2003 | Alexandre et al. |
| 2004/0015125 A1 | | 1/2004 | Alexandre et al. |
| 2004/0215149 A1 | | 10/2004 | Hjertman |

FOREIGN PATENT DOCUMENTS

| DE | 102 11 473 A | 10/2003 |
| FR | 2 815 544 A1 | 4/2002 |
| WO | WO 01/58512 A1 | 8/2001 |
| WO | WO 01/89614 A1 | 11/2001 |
| WO | WO 01/97884 A1 | 12/2001 |

* cited by examiner

*Primary Examiner*—Matthew F Desanto
(74) *Attorney, Agent, or Firm*—Oliff & Berridge, PLC

(57) ABSTRACT

The invention relates to needleless syringe for injecting an active liquid principle. The inventive syringe comprises a container (3) closed by a movable shutter and containing the injectable liquid. Said container is initially insulated from an injector-receptacle provided with a cylinder bore (10) in which a downstream shutter is arranged and which comprises at least one protuberance reducing the section with respect to the upstream opening of the bore. The aim of said invention is to damp and prevent the downstream shutter bounce when it is disposed in the bore (10) of the receptacle.

8 Claims, 2 Drawing Sheets

NEEDLELESS SYRINGE PROVIDED WITH A DAMPING INJECTOR RECEPTACLE

The present invention concerns the field of prefilled and disposable needleless syringes; such syringes are used for intradermal, subcutaneous and intramuscular injections of liquid active principle intended for therapeutic use in human or veterinary medicine.

A first imperative for prefilled syringes is that of compatibility in the long term, generally three years, between the liquid active principle and the reservoir that contains it. Another imperative, associated with the prefilling method, is that of having a transparent reservoir in order to be able to carry out the regulatory verification of correct filling of the reservoir before it is fitted in the syringe. These imperatives lead to the production of a reservoir that is substantially transparent and is made of a material which is compatible with the active principle for the desired length of time: this material is generally glass for pharmaceutical use: glass type I or II.

The initial phase of the injection is critical for the penetration, into the skin, of the jet or jets of liquid, depending on whether the syringe has one or more injection conduits. The latter configuration is favorable for reducing pain. The final bioavailability depends on the correct implementation of this initial phase; it assumes a rapid acceleration of the liquid in the injection conduits without the multiple reverberation of the jets when there is too great a pressure surge to achieve this rapid acceleration.

Patent application WO 01/58512 describes a needleless syringe comprising a reservoir which is closed off by displaceable upstream and downstream obturators and which encloses a liquid active principle; said reservoir is initially isolated from an injector or receptacle comprising at least two injection conduits situated on its outer lateral face, and a blind central bore in which the downstream obturator will lodge in such a way as to free the inlets of the injection conduits upon displacement of the movable assembly comprising downstream obturator, active principle and upstream obturator, under the action of a drive device for carrying out the injection.

The problem to be addressed with this type of syringe is that of damping the impact of the movable assembly when the downstream obturator comes into contact with the bottom of the bore of the receptacle, and also that of avoiding the rebound of said downstream obturator after this impact. The aforementioned application proposes solutions to this problem, but the person skilled in the art is always looking for alternative and novel solutions.

The present invention concerns a needleless syringe comprising a body that accommodates a cylindrical reservoir which is closed off by a displaceable upstream obturator and by a displaceable downstream obturator and which encloses an active principle, and comprising, downstream of this, a receptacle with at least one peripheral injection conduit, said receptacle bearing on the reservoir and comprising a central bore in which the downstream obturator lodges when it is brought into contact with the bottom of the bore of said receptacle by the operation of a drive means that displaces the assembly of upstream obturator, liquid and downstream obturator, said syringe being characterized in that the lateral wall of the bore comprises at least one protuberance reducing the cross section relative to the upstream opening of the bore, and in that the internal volume of said bore permits clearance of the inlets of the peripheral conduits when the downstream obturator is lodged in the central bore.

It should be noted that the central bore can be blind with a substantially flat bottom or can comprise at least one spike on which the downstream obturator will deform and tear. The central bore can also comprise, at its bottom, at least one orifice. Moreover, this orifice can be calibrated in such a way as to limit the flow of air driven by the downstream obturator and thus participate in a pneumatic braking of the movable assembly.

In this application, the qualifying word downstream designates any component near the injection site or any component part directed toward this injection site, this site being the patient's skin. By contrast, the qualifying word upstream will be used for any component remote from the injection site or for any component part directed away from this site. Thus, the receptacle comprises a downstream face directed toward the patient's skin, and an upstream face which is directed the other way and bears on the reservoir; these downstream and upstream faces are connected by a lateral face.

In this invention, liquid active principle, or medicament, will be understood principally as meaning a more or less viscous liquid, or a mixture of liquids, or a gel. The active principle can be a solid dissolved in a suitable solvent for injection. The active principle can be a solid in powder form in more or less concentrated suspension in a suitable liquid. The granulometry of the solid active principle must be adapted, as must the shape of the conduit, to avoid blockages.

The substantially cylindrical reservoir is made of glass type I or type II; but it can be made of any other material that is transparent and compatible with the active principle. The upstream and downstream faces of the reservoir are substantially flat, the planes containing them being perpendicular to the axis of symmetry of the reservoir. The upstream and downstream faces bear on the body of the syringe and the receptacle, respectively. The bearing surfaces of these two components comprise seals whose characteristics will be explained in detail below.

An injection conduit runs the entire height of the receptacle from the upstream face to the downstream face. When there are at least two of them, the injection conduits are called peripheral, because they are disposed in the receptacle around the central bore. They communicate with said central bore only via inlets that are described below. The injection conduit has a cross section that varies from upstream to downstream, on the one hand for reasons associated with its production, and on the other hand in order to obtain a jet that is sufficiently fine and rapid to penetrate the patient's skin to the desired depth. In general, the injection conduits are identical, distributed equally around the blind central bore and have axes parallel to the receptacle axis, but they can also be different. When there is little active principle to inject, a single injection conduit is sufficient.

The drive means which will act on the upstream obturator and the whole of the movable assembly can be a mechanical drive: release of a compressed spring, or of the pneumatic type: release of compressed gas, or pyrotechnic: release of combustion gas.

The syringe functions in the following way: the drive means will act on the upstream obturator and displace the assembly of upstream obturator, liquid and downstream obturator, because the liquid is incompressible. The downstream obturator is displaced and lodges in the central bore of the receptacle until contact is made with the bottom of said bore. The volume of this bore is such that when the downstream obturator is in contact with the bottom of said bore, the inlets of the injection conduits, on the periphery of the bore of the receptacle, are freed; the liquid is driven back there and is injected by the movement of the upstream obturator, which continues until the reservoir is emptied: the upstream obturator is then in contact with the downstream obturator.

The inlet of an injection conduit, situated on the upstream face of the receptacle, comprises a countersink positioned and preferably centered on the injection conduit, and a radial channel connecting said countersink to the central bore of said receptacle.

Advantageously, the circular protuberance reducing the cross section of the bore is formed by the succession of two truncated cone parts when penetrating into the bore and following the displacement of the downstream obturator. The truncated cone situated at the upstream end is convergent and is connected to a divergent truncated cone either as far as the bottom of the receptacle or to a cylindrical portion connecting to the bottom of the receptacle. The convergent truncated cone part brakes the downstream obturator, then the divergent truncated cone part following it has the role of blocking the downstream obturator in the bore when it is engaged there.

In a second embodiment, the reduced cross section is obtained by superposition of several circular protuberances, such as have been described above, along the full height or part of the height of the central bore, for example by a succession of several alternately convergent and divergent truncated cones. In a preferred embodiment, the divergent truncated cones can be reduced to an abrupt widening to the inlet diameter of the bore, which will give a sawtooth profile to the protuberances of the bore.

In a third embodiment, the protuberance can be a helical projection in the form of an internal threading that winds across the lateral wall of the central bore, the thread having a suitable cross section.

In a fourth embodiment, the protuberances are projections along a generatrix of the wall of the blind central bore. Said projections are preferably equally distributed all around the bore, and these projections are advantageously formed in line with the zones where the injection conduits are located. Said projections either have an ovoid bead shape or are notched, several small projections being formed in succession along the generatrix. These protuberances can in some way be part of the above-described protuberances which are then not entirely circular but are only sectors around a generatrix of the bore.

The present invention, applied to a prefilled disposable syringe, has the advantage of making it possible to separate two parts of the device. A part which will be called the pharmaceutical part comprising the body and the reservoir with the displaceable upstream and downstream obturators and if appropriate the injector receptacle: this subassembly will be able to be processed under the conditions applying in the pharmaceutical industry, in particular as regards sterilization and asepsis. This subassembly will be integrated with the rest of the syringe whose elements have been joined together, this assembling being done under less stringent conditions than those associated with the pharmaceutical industry.

When the downstream obturator is lodged in the bore of the receptacle, the syringe becomes very difficult to reuse. This arrangement thus also has the advantage of preventing reuse of said syringe for purposes different than the initial therapeutic use.

Finally, this configuration has the advantage of avoiding possible leaks of liquid via the injection conduits before the injection is performed. This is because the device is frequently shaken, as is recommended, in order to examine the turbidity of the liquid or to homogenize the mixture when the liquid comprises particles in suspension. The fact that the active principle is isolated, before injection, affords ultimate protection against this risk of loss.

The invention is set out in detail below with the aid of figures representing different specific embodiments of the invention.

FIG. 1 shows, in a partial longitudinal section, a syringe according to the invention; it is shown vertically, the injection system directed toward the bottom, which will be the downstream end.

Figure 1:
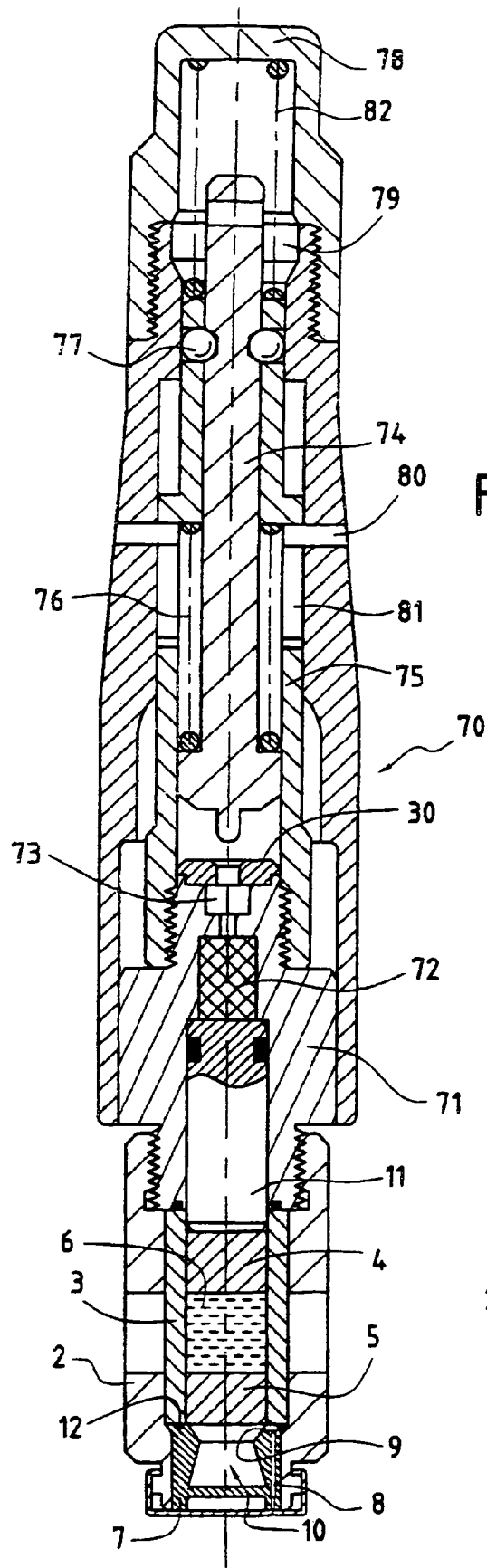
FIG. 1 shows a longitudinal section through a syringe according to a first embodiment of the invention.

The syringe 1 comprises a body 2 which houses a reservoir 3 containing the liquid active principle 6. Placed at the downstream end of the body 2 there is a receptacle 7 comprising, for example, three injection conduits, such as the conduit 8. The injection system is covered by an external protection in order to ensure asepsis of the syringe: this protection comprises an elastomeric membrane applied on the outer face of the injector via a fine metal protective seal, crimped about this end of the syringe. This protection will be removed before the injection. At its opposite end, the body 2 of the syringe is fixed to a drive means 70 which, in this example, is a pyrotechnic gas generator, which will be described below. The reservoir 3 bears on the body 71 of the drive means 70, the leaktightness being ensured by an O-ring seal.

The body 2 of the syringe comprises two diametrically opposite windows for viewing the active principle contained in the reservoir 3: these are simply two oblong openings in the body. Arranged downstream of the body 2 of the syringe, and engaged in a bore of suitable shape, there is a receptacle 7, which will be described below. A reservoir 3 made of glass is positioned bearing on this receptacle 7 and centered downstream of the body 2; this reservoir is a tube. Upstream, the body 2 of the syringe receives the body 71 of the drive means which is centered about the other end of the reservoir. The reservoir 3 is essentially a tube that is closed off at its two ends by displaceable upstream 4 and downstream 5 obturators; these obturators are preferably plunger stoppers commonly used in syringes: these are components that are obtained by molding of elastomers which are compatible with the active principle over a long period of time: each component incorporates the functions of plunger and leaktightness via flanges or lips (not detailed in the figures). The elastomers normally used for the production of these components are, for example, chlorobutyl or bromobutyl, whose Shore hardness is set between about 45 and about 70. These components can be surface-treated, in particular to facilitate their displacements in the tubular reservoir. When it is free, the plunger stopper has a diameter greater by about 10 percent than the internal diameter of the tube which is going to receive it, the height of the plunger stopper being about 0.5 to 0.8 times this diameter. When the plunger stopper is engaged in the tube, because of the deformations its height is equal to about 0.6 times to about 1.0 times the internal diameter of the reservoir.

In this example (see also FIG. 2), the receptacle 7 is a component with a cylindro-conical external shape which comprises a central bore 10 in which the downstream obturator 5 will lodge. On its periphery, the receptacle comprises three injection conduits, only one of which, labeled 8, can be seen in this cross section. The injection conduits, such as the conduit 8, extend the entire height of the receptacle 7 from the upstream face to the downstream face. They communicate with the central bore 10 by way of inlets 9 formed by a countersink positioned on the injection conduit and a radial channel connecting said countersink to the central bore 10. The free volume of the blind bore 10 of the receptacle 7 is equal to that of the downstream obturator 5. When the downstream obturator 5 has reached the bottom 7a of the receptacle, the inlet 9 (toward reservoir 3) of the injection conduit 8 is brought into communication with the liquid 6; the liquid flows with a speed corresponding to the pressure transmitted by the upstream obturator 4.

In this embodiment, the drive means acts on the upstream obturator by way of a plunger 11 with an effective cross section equal to that of the upstream obturator 4. This plunger 11 is in contact with the upstream obturator 4, and there is therefore no shock or pressure surge effect at the start of functioning. By virtue of its leaktight system, this plunger 11 prevents the gases produced by the combustion of the charge 72 from coming into contact with the upstream obturator and thus prevents possible damage to the latter and escape of gas toward the active principle contained in the reservoir. This plunger 11, of a suitable color, can also serve as an operation indicator by appearing in the viewing windows of the body 2 of the syringe.

We will now describe the main elements of the pyrotechnic generator 70. It comprises, in the body 71 above the plunger, a pyrotechnic charge 72 whose combustion is initiated by a primer 73 impacted by a striker 74. The primer 73 is housed in a primer holder. In the initial position, the striker 74 is retained in the striker guide 75, made integral by screwing to the body 71, by means of at least one ball, such as the ball 77, partially engaged in a groove of the striker. The striker device comprises a push button 78 with a groove 79 and an internal spring 76.

The push button 78 slides on the outside of the striker guide 75 and it is held by stubs 80 which move in lateral grooves 81. This push button 78 is in this case the trigger member.

In order to initiate the combustion of the pyrotechnic charge 72, it is of course possible, without departing from the scope of the invention, to use initiation devices other than the striker device described here. Without wishing to be exhaustive, we will cite, as examples, initiation devices with an electric battery or piezoelectric initiation devices.

If appropriate, the pyrotechnic gas generator can be replaced by a gas generator formed by a reservoir of compressed gas closed by a valve which can open quickly. The trigger member will open said valve, and the compressed gases of the reservoir will expand and act on the thrust means.

After removing the asepsis stopper, and having placed the downstream face of the injector on the skin of the subject who is to be treated, the operator presses the push button 78, which is driven down and compresses the spring 82. The push button is displaced until the groove 79 arrives level with the groove of the striker 74, the balls, such as the ball 77, retaining the striker 74, move into the groove 79 and release the striker, which, propelled by the spring 76, will violently impact the primer 73, whose initiation fires the pyrotechnic charge 72. The striker 74 bearing on the primer holder 30 ensures that the primer is held in place and ensures leaktightness: the gases of combustion do not ascend toward the push button. The combustion of the pyrotechnic charge will produce gases that act on the plunger 11.

FIG. 1 shows a syringe, according to the invention, in the shape of a pen: all the elements have the same central axis but are superposed. Without departing from the scope of the present invention, other configurations are conceivable, for example the drive part can be at a certain angle to the reservoir/receptacle part in order to arrive at more compact shapes, such as the one described, for example, in the patent application FR 2 815 544.

Figure 2:
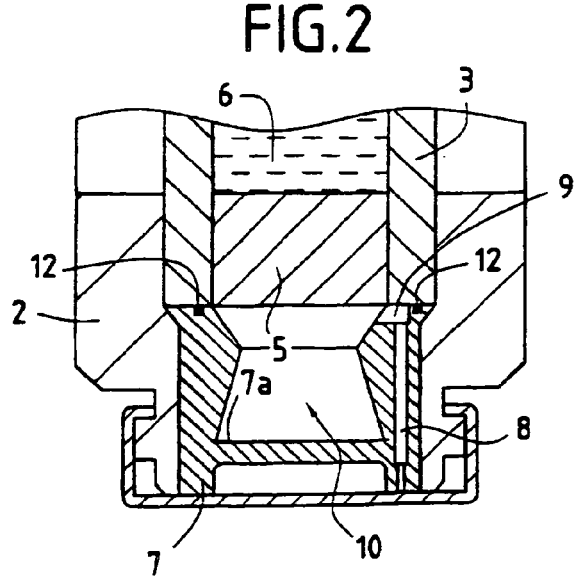
FIG. 2 shows an enlarged view of the downstream part of said syringe.

FIG. 2 is an enlarged representation of the downstream part of the syringe shown in FIG. 1.

For the receptacle 7, the narrowing of the cross section of the bore 10 by a circular protuberance is achieved by head-to-tail superpositioning of two truncated cones. A first, convergent truncated cone when moving axially from upstream to downstream: the inlet diameter at the upstream end of this truncated cone is equal to the internal diameter of the reservoir 3, the final diameter of this truncated cone is equal to about 0.8 times the inlet diameter, and the height of the truncated cone is equal to about 0.2 times the inlet diameter. This first truncated cone is joined, either directly or via a small cylindrical portion, to a divergent truncated cone as far as a part with a diameter at most equal to that of the reservoir 3; the height of this second truncated cone can occupy the entire remaining height of the bore 10 or only part of this height, the rest being a cylindrical portion connecting to the bottom 7a of the receptacle 7. The connections between the different parts are preferably rounded so as to avoid sharp edges tearing the downstream obturator 5 when it engages in the bore and passes these connection zones.

The protuberance reducing the cross section, as described above, can be produced in different ways.

For example by direct molding of the receptacle with a deformable or demountable core, but this technique does not lend itself very well to production of a large number of components at a high production rate.

The receptacle is preferably produced in two parts by molding of two components: one representing the receptacle, but with a cylindrical central bore, and the second being an insert with two truncated cones. The two components are then joined together by force-fit or adhesive bonding using any suitable method.

In the figures that follow, only the syringe receptacle will be shown in a partially section perspective view, without going into detail concerning the way said receptacle is mounted in the body of the syringe. By convention, the upstream face of the receptacle, as defined above, is the one directed upward from the page. This upstream face generally comprises a circular or almost circular sealing groove which receives an O-ring seal, or a bi-injection-molded seal if the receptacle is produced by injection molding. On the front face, each injection conduit is continued by a small protuberance which serves to support the receptacle on the patient's skin. We will not return to these particulars in each case.

Figure 3:
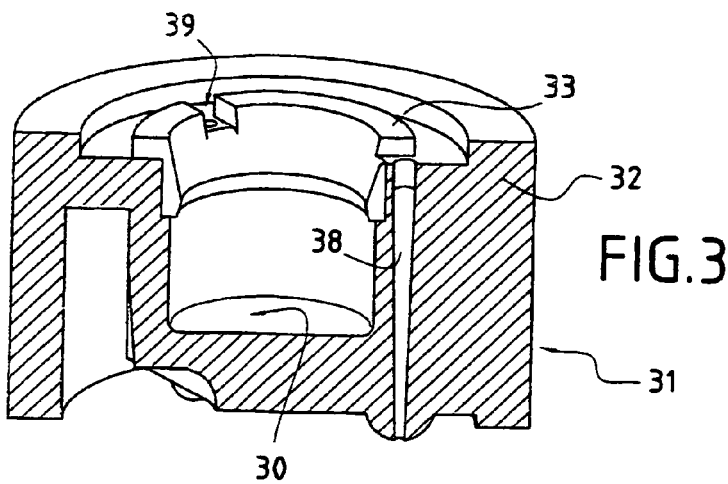
FIG. 3 shows a perspective and partially sectioned view of another example of the invention according to the first embodiment, but here obtained by assembling two parts or components.

FIG. 3 shows an illustrative embodiment of a receptacle 31 with a single circular protuberance produced by joining together of two elements. A first main element 32 essentially constitutes the receptacle with an almost cylindrical central bore 30 and the peripheral injection conduits 38. The second element 33 is a hollow insert whose opening has two truncated cone shapes, with a part converging from the upstream face of the receptacle. This insert comprises radial indents 39 coincident with inlets of the injection conduits. Formed between the insert 32 and the main element 31 there is a circular groove which will receive an O-ring seal. The insert fitted in the main element comes into abutment against a shoulder of the bore. In this example, the protuberance does not take up the entire height of the blind bore.

Figure 4:
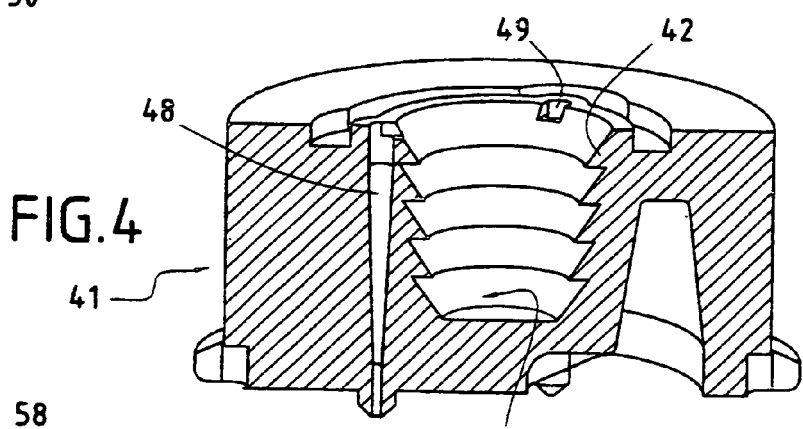
FIG. 4 is a perspective and sectioned schematic view of a receptacle formed according to a second embodiment by superposition of several circular constrictions along the full height of the bore.

FIG. 4 is a schematic view of the central bore 40 of a receptacle 41 according to a second embodiment of the invention. The bore comprises, superposed on one another, several protuberances 42 formed by a convergent truncated cone part and by an abrupt widening to the opening diameter of the bore, which arrangement gives a sawtooth appearance to a longitudinal section of the bore.

Figure 5:
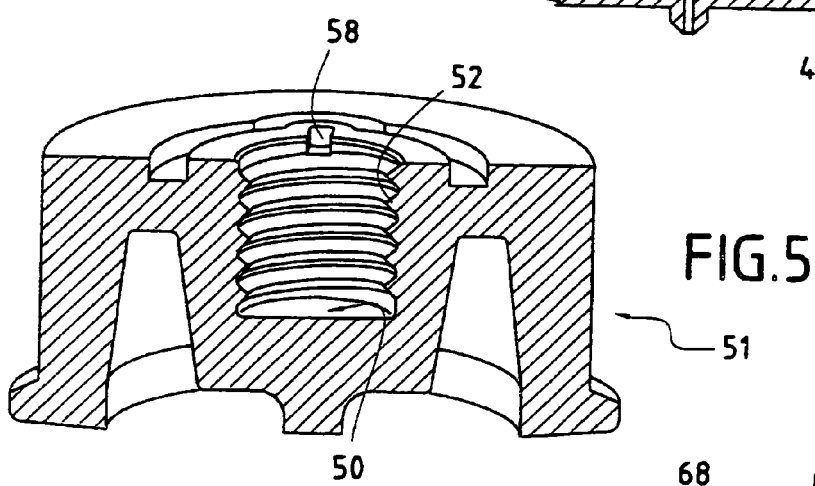
FIG. 5 shows a perspective view of a third embodiment of the invention with an internally threaded bore.

FIG. 5 likewise shows a receptacle 51 whose protuberance 52 in the central bore 50 is an internal thread as far as the bottom of the bore: here the internal thread is a thread of simple symmetry.

Figure 6:
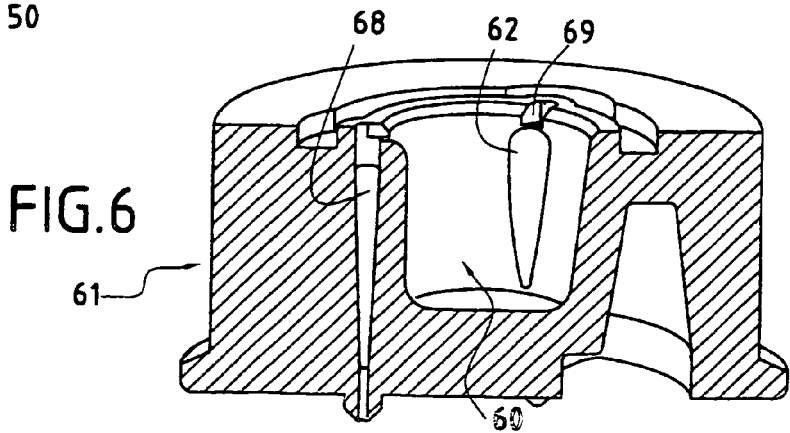
FIG. 6 shows a fourth embodiment of the invention, the protuberances being ovoid projections along lateral generatrices of the bore.

FIG. 6 shows an example of a receptacle according to a fourth embodiment of the invention. The receptacle 61 comprises a slightly frustoconical central bore 60 and peripheral injection conduits 68. In line with these injection conduits, ovoid projections 62 can be seen on the lateral surface of the bore: these projections are essentially oriented along the generatrices of the lateral surface of the bore. These are projections, equally distributed like the injection conduits, that form the narrowing of the bore. It will be noted that on the upstream face of the receptacle there is an almost circular sealing groove with lobes which run round the inlets 69 of the injection conduits 68. This sealing groove receives a multi-lobe seal or preferably the seal is injected after the receptacle has been produced by a first injection. This bi-injection technique is already known.

The invention claimed is:

1. A needleless syringe comprising a body (2) that accommodates a cylindrical reservoir (3) which is closed off by a displaceable upstream obturator (4) and by a displaceable downstream obturator (5) and which encloses an active principle (6), and comprising, downstream of this, a receptacle (7, 31, 41, 51, 61) with at least one peripheral injection conduit (8, 38, 48, 58, 68), said receptacle bearing on the reservoir and comprising a bore (10, 30, 40, 50, 60) in which the downstream obturator (5) lodges when it is brought into contact with the bottom (7a) of the bore of said receptacle by the operation of a drive means (70) that displaces the assembly of upstream obturator, liquid and downstream obturator, said syringe being characterized in that the lateral wall of the bore comprises at least one protuberance reducing the cross section relative to the upstream opening of the bore, and in that the internal volume of said bore permits clearance of the inlets of the peripheral conduits when the downstream obturator is lodged in the bore (10, 30, 40, 50, 60).

2. The needleless syringe as claimed in claim 1, characterized in that the central bore (10) comprises a single circular protuberance.

3. The needleless syringe as claimed in claim 2, characterized in that said circular protuberance is the superposition of two truncated cones converging then diverging from the upstream face of the receptacle.

4. The needleless syringe as claimed in claim 1, characterized in that the central bore comprises several superposed circular protuberances over at least part of the height of the bore (10).

5. The needleless syringe as claimed in claim 4, characterized in that said protuberances are a superposition of several truncated cones converging and diverging over at least part of the height of the bore.

6. The needleless syringe as claimed in claim 1, characterized in that the central bore comprises at least one protuberance (62) along a generatrix of the bore.

7. The needleless syringe as claimed in claim 6, characterized in that said protuberances are distributed in line with the injection conduits.

8. The needleless syringe as claimed in claim 1, characterized in that the central bore comprises a helical protuberance in the form of an internal threading (52).

* * * * *